(12) United States Patent
Giffels et al.

(10) Patent No.: US 6,180,837 B1
(45) Date of Patent: Jan. 30, 2001

(54) PROCESS FOR THE CATALYTIC ENANTIOSELECTIVE REDUCTION OF KETONES

(75) Inventors: Guido Giffels, Bonn (DE); Marcel Felder, Dottikon (CH); Udo Kragl, Kritzmow (DE); Christian Wandrey, Julich (DE); Andreas Bommarius, Frankfurt (DE); Carsten Bolm, Aachen (DE); Nadine Derrien, Cambridge (GB); Karlheinz Drauz, Freigericht (DE)

(73) Assignees: Degussa-Huels AG; Forschungszentrum Julich GmbH, both of (DE)

( * ) Notice: Under 35 U.S.C. 154(b), the term of this patent shall be extended for 0 days.

(21) Appl. No.: 09/308,211

(22) PCT Filed: Nov. 20, 1997

(86) PCT No.: PCT/EP97/06479

§ 371 Date: Jul. 13, 1999

§ 102(e) Date: Jul. 13, 1999

(87) PCT Pub. No.: WO98/22415

PCT Pub. Date: May 28, 1998

(30) Foreign Application Priority Data

Nov. 20, 1996 (DE) .............................. 196 47 892

(51) Int. Cl.$^7$ ................................. C07C 29/143
(52) U.S. Cl. ........................................... 568/814
(58) Field of Search ...................... 568/813, 814

(56) References Cited

U.S. PATENT DOCUMENTS 3,883,580 * 5/1975 Solodar .

OTHER PUBLICATIONS

Francot et al A polymer–bound Oxazaborolidine Catalyst: Enantioselective Borane Reductions of ketones' Tetrahedral Asymmetry, vol. 6 No. 11 pp. 2755–2766 (found in the PCT report), Nov. 1995.*
CA:124:144896 abs of React. Funct. Polymer by Caze 26 (1–3) pp. 85–94, 1995.*
CA:125:81151 abs of Recl Trav Chim Pays–Bas by Kruse 115(4) pp. 239–243, 1996.*
CA:124:311470 abs of Biochem Eng 3, Int Sym 3rd by Kruse pp. 181–3, 1995.*

* cited by examiner

Primary Examiner—Jean F. Vollano
(74) Attorney, Agent, or Firm—Selitto & Associates

(57) ABSTRACT

The invention involves a procedure for the catalytic enantioselective reduction of ketones to chiral alcohols. Heretofore, this reaction was carried out batch-wise. Because, in this procedure, one utilizes a catalyst increased in size with polymer, it is possible to carry out the reaction in a quasi-continuous manner in a membrane reactor. In contrast to the state of the art, one thus dramatically increases the operative life of the catalyst.

7 Claims, 2 Drawing Sheets

CATALYST

R=POLY-O, DENDRIMER

PROCESS FOR THE CATALYTIC ENANTIOSELECTIVE REDUCTION OF KETONES

This is the national phase of PCT/EP97/06479, filed Nov. 20, 1997, now WO 98/22415.

FIELD OF THE INVENTION

The invention involves a procedure for the catalytic enantioselective reduction of ketones to chiral alcohols.

DISCUSSION OF THE PRIOR ART

Chiral alcohols are, for example, important intermediates in the pharmaceutical industry. There is therefore a great interest in procedures which make these compounds available in high optical purity. In conjunction therewith, catalytic procedures are particularly advantageous since with the use of small quantities of the generally expensive chiral auxiliaries, a multiple of the chiral product can be produced.

A procedure of this type is, for example, the oxazaborolidine-catalyzed reduction of ketones to chiral alcohols with boranes, for example, borane dimethylsulfide complex, or borane tetrahydrofuran complex (see for example, Wallbaum, S. and Martens, J., in *Tetrahedron Asymmetry* 3 1992, 1475–1504). The reaction is set forth in FIG. 1. This method provides chiral alcohols in good to very good yield and enantiomeric excess (enantiomeric excess= ee). In this manner a series of pharmaceutically relevant compounds can be produced.

In general, for the achievement of an optimal enantiomeric excess, between about 5 to 10 mol/% of the catalyst (relative to the ketone) is needed. A minimization of the catalyst expenses can therefore make a crucial contribution to the cost advantage of the procedure.

Many attempts have been undertaken to raise the cycling number (mols of product per mol of spent catalyst). Thus for example, the oxazaborolidines utilized as catalysts were immobilized on insoluble carriers. These heterogeneous oxazaborolidines were obtained by coupling the utilized chiral amino alcohol ligands to a cross-linked polystyrene resin with boric acid groups (Franot, et al., in *Tetrahedron Asymmetry* 6, 1995, 2755– 2766). The thus obtained heterogeneous catalyst can be filtered off after the reaction and charged anew. Already during carrying out of the third reaction cycle, the enantiomeric excess achieved, drops under 80% so that further provision of the catalyst is no longer meaningful. Therefore by this means, the cyclic number can only be negligibly raised from 10 (corresponding to 10 mol % catalyst) up to 20 to 30.

SUMMARY OF THE INVENTION

The purpose of the present invention was to solve the technical problem of making a procedure available which enables the effective exploitation of the chiral catalyst.

This problem is solved by the present invention in that the catalytic enantioselective reduction of ketones to chiral alcohols with a molecular weight increased catalyst is carried out in a membrane reactor. By means of this procedure in accordance with the present invention, one is surprisingly able to raise the cycling number by a factor of 10 to 120 moreover without loss of the enantioselectivity of the charged catalyst. Moreover, this procedure delivers the chiral alcohols in enantiomeric excess of 90% ee. The retention, as well as the separation of the soluble catalyst by the membrane such as for example, an ultra or nanofiltration membrane, has furthermore the advantage that the reaction can be carried out in a homogeneous solution without material transportation limitations.

As catalyst, the charging of a chiral oxazaborolidine is particularly advantageous. As catalysts however, there may also be utilized transition metal compounds such as for example titanates, which then, via the chiral ligands, for example diol-ligands, can be coupled to the compound utilized for molecular weight increase.

The preferred oxazaborolidine of the present invention has two possible positions for molecular weight enlargement. A coupling of this substance to the compound utilized in molecular weight increase can occur either via an amino alcohol or a boron acid. Preferably the oxazaborolidine in accordance with the present invention, is coupled to the molecular weight increasing compound via the chiral amino alcohol.

DISCUSSION OF THE PREFERRED EMBODIMENTS

Figure 1:
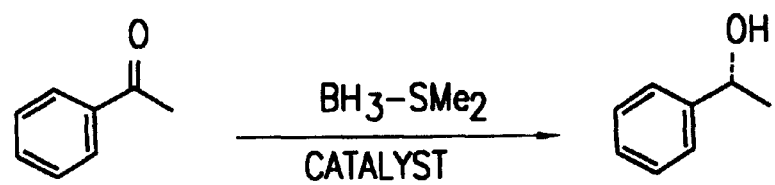
FIG. 1 is a flow diagram of the prior art.
Figure 1:
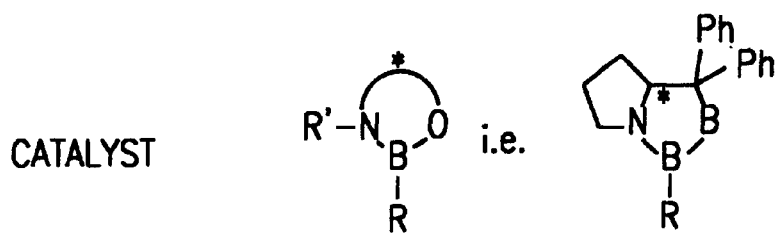
Figure 2:
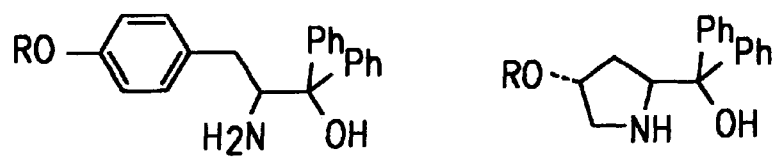
FIG. 2 illustrates certain preferred ligands.

As ligands, in principle all the chiral amino alcohols may be utilized which have a) (further) functional group which enables the binding, in particular however, tyrosinol or hydroxy proline derivatives are desirable. Specifically, diphenyl tyrosinol and diphenyl hydroxyprolinol (FIG. 2) achieve very good results.

For molecular weight enlargement, there is suitably utilized a polymer, in particular a polystyrene or polysiloxane, a molecular weight enlargement of the catalyst as well as its precursors can also be achieved by the coupling of the appropriate compounds, for example, to dendrimers. The coupling occurs in that a ligand is coupled to a ready poly or dendrimer via a functional group not required for catalysis. Alternatively, the ligand can also be provided with a polymerizable functionality which can become copolymerized with another monomer.

The substances taking part in the catalytic enantioselective reduction of the present invention should preferably be homogeneously soluble in organic solvents.

The active oxazaborolidine catalyst is formed from the chiral amino alcohols in the presence of (utilized for reduction) borane ($BH_3$) under the splitting off of two equivalents of hydrogen. This can either take place in situ in the reactor or separately before the catalyst is washed into the reactor.

Also, the reaction of the amino alcohol ligands with different boron acids or boron acid derivatives can be utilized for the formation of oxazaborolidines. The molecular weight increased catalysts are then charged to a suitable membrane reactor for the continuously driven enantioselective reduction of prochiral ketones.

Figure 3:
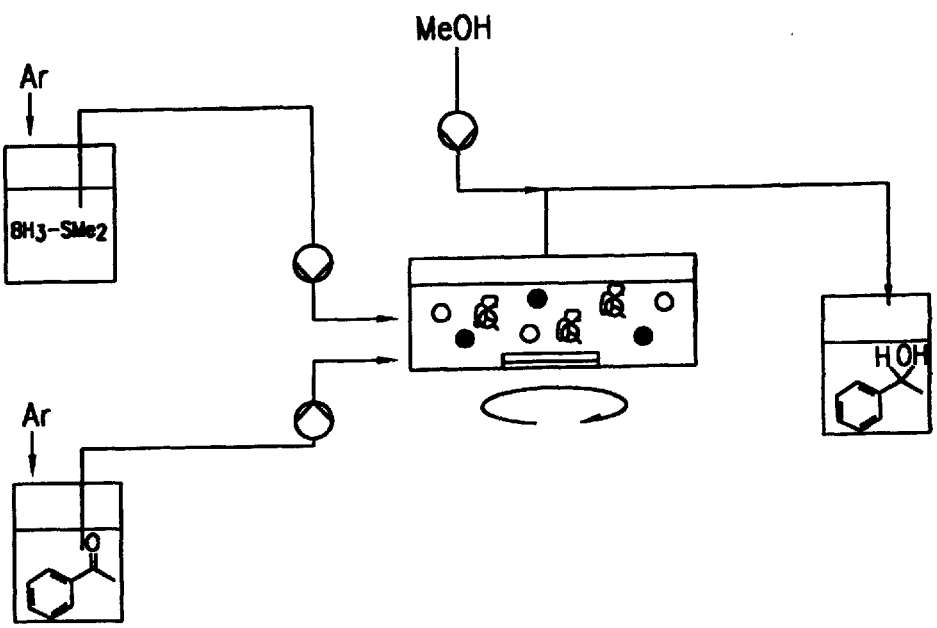
FIG. 3 is a schematic flow diagram of the process of the present invention.

The flow diagram of such a reactor construction is set forth in FIG. 3. The two educts, the borane as well as the ketone, are dissolved in a suitable organic solvent, in particular toluene or tetrahydrofluran (THF) pumped via a pump into the membrane reactor from reserve containers standing under a protective gas to the exclusion of oxygen and air humidity. This comprises for example a stirring cell with a solvent stable ultra or nanofiltration membrane (flat membrane). It is also possible to utilize hollow fiber modules. At the reactor exit, the reaction mixture (via a T-piece) is quenched with methanol in order to liberate the produced chiral alcohol and perhaps destroy any surplus borane.

Figure 4:
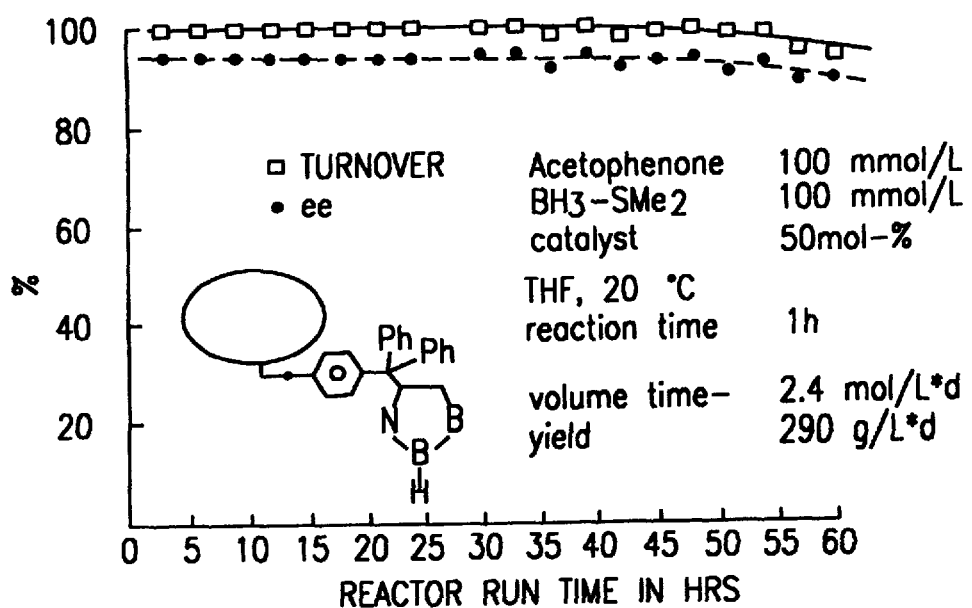
FIG. 4 is a plot of turnover and enantioselective excess against reactor run time.

Such a reactor can be run in a stable manner for several days, that is to say, over long contact times. An exemplary reaction run is set forth in FIG. 4. Very high turnovers and enantiomer excesses are achieved in accordance with the procedures of the present invention. Thus, a very high space—time yield is achieved, which is an important criterion for the economic viability of the process.

In comparison to the utilization of free—or also heterogeneous catalysts in a batch reactor, a large part of the preparation time is avoided by the use of the continual process mode. In comparison to the situation with a similar batch reactor, the large amounts of borane containing reaction solution and the dangers connected therewith are avoided.

The work-up of the product solution in comparison to production in a batch reactor, is substantially simplified since the catalyst need no longer be separated out. The removal of surplus borane proceeds in a simple manner. It can either be distilled off as a boric acid trimethyl ester subsequent to methanol quenching, or it is readily available after aqueous work-up as boric acid in alkaline extraction. Through the high turnovers, that is to say, through approximately quantitative conversion of the ketone into the alcohol and avoidance of appearance of by-products, the purification of the accrued product is simplified if not actually superfluous.

By utilization of the process of the present invention, a plurality of ketones can be economically converted into the chiral alcohols. Through the use of molecular weight increased homogeneous solutions of oxazaborolidines, the cycling number of these catalysts can be substantially increased without, as with other procedures, acceptance of a reduction of the enantioselectivity. Rather, surprisingly in part, even better enantioselectivity is noticed compared to free catalysts in a batch reactor. Hereinbelow, the invention will be further explained by means of examples.

EXAMPLES

Example I

Formation of Polymer Increased α,α-Diphenyltyrosinol

To a solution of 86° mmol phenyl magnesium bromide, produced from 22 g magnesium and 90 ml bromobenzene in 900 ml tetrahydrofuran (THF), 21 g of tyrosine ethylester hydrochloride (85 mmol) were added batch-wise at 0° C. and stirred at room temperature overnight. Subsequently, hydrolysis with ammonium chloride solution is carried out. The organic phase is separated and the aqueous phase extracted four (4) times with ethyl acetate. The combined organic phases are dried over sodium sulfate and the solvent distilled off. Double recrystallization from ethanol gives 17 g of (S)-2-amino-3-(4-hydroxyphenyl)-1,1-diphenyl propan-1-ol (=α,α-diphenyl tyrosinol, 62% yield). This is reacted in dimethyl formamide with 1 equivalent of sodium hydride and after cessation of $H_2$ generation (circa 1 hour) is reacted with an equimolecular amount of vinyl benzyl chloride. After stirring for 5 hours at room temperature, the reaction mixture is poured into an excess of water and the white precipitate filtered off and recrystallized from ethanol to yield (S)-2-amino-3-(4-(vinyl phenylmethoxy)-1,1-diphenylpropan-l-ol in approximately 45% yield.

13 g of this monomer (29.9 mmol) are copolymerized with 5 equivalents of freshly distilled styrene (150 mmol) under the utilization of 275 mg of azobisisobutyronitrile as radical initiator in 220 ml of toluene. The mixture is stirred for 50 hours at 60° C. under argon. The polymer is then precipitated in methanol to yield 15.1 g of polymer, corresponding to a 53% yield. The mean molecular weight as determined by gel permeation chromatography is 13,800.

Example II

A Continuous Reduction in a Membrane Reactor

The reactor arrangement for the continuous enantioselective reduction corresponds to the scheme set forth in FIG. 3. As reserve containers, there are utilized conventional 3-necked flasks which are placed under protective gas. Teflon hoses are utilized as conduits. As pumps, there are utilized Pharmacia P-500 Reciprocating Piston Pumps. The membrane reactor comprises a polypropylene flat membrane cell with 10 ml reaction volume, stirred with a magnetic stirrer. It is equipped with a solvent-stable nanofiltration membrane MPF 50 (manufactured by Membrane Products).

The pump and the reactor are rinsed with absolute (water-free) THF. Subsequently, 0.5 mmol of the polymer bound ligands corresponding to 50 mol % catalyst (dissolved in THF) are pumped into the membrane reactor via one of the pumps. The reactor is now rinsed for 1–2 hours with a solution of borane dimethyl sulfide ($BH_3$—$SMe_2$) in THF (200 mmol/L, 10–20 ml/hr). Thereby there is formed the oxazaborolidine from the amino alcohol held back in the membrane reactor.

Then a solution of 200 mmol/L of acetophenone in THF is dosed into the reactor via the second pump. The flows of both pumps are set to 5 ml/hr. The contact time T=1 hour, and the initial concentration of ketone and borane are each 100 mmol/L. Via T-piece at the reactor exit, quenching takes place with 4 ml/hr. of methanol. The reaction product is collected in a fraction collector. Turnover and ee are measured gas chromatographically. A corresponding reactor sequence is reproduced in FIG. 4. It shows that the reactor can be stably run for a substantial length of time and turnovers of up to 100% can be obtained. Thus the process of the present invention delivers the sought enantiomeric excess of equal to or greater than 90% ee.

What is claimed is:

1. A process for the catalytic enantioselective reduction of ketones to chiral alcohols, wherein the reaction is carried out in a membrane reactor comprising an organic solvent stable ultra or nanofiltration membrane utilizing a catalytic agent soluble in an organic solvent comprising a chiral catalyst coupled to a polymer or a dendrimer.

2. The process in accordance with claim 1, wherein the chiral catalyst is a chiral oxazaborolidine.

3. The process in accordance with claim 1, wherein the oxazaborolidine is coupled to a polymer via a chiral amino alcohol moiety attached to said polymer.

4. The process according to claim 3, wherein the chiral amino alcohol moiety is diphenyl tyrosinol or diphenyl hydxroxy proline.

5. The process in accordance with claim 1 wherein the chiral catalyst is coupled to a polymer.

6. The process in accordance with claim 5, wherein the polymer is a polystyrene or a polysiloxane.

7. The process in accordance with claim 1 wherein the chiral catalyst is coupled to a dendrimer.

* * * * *